US008444963B2

(12) United States Patent
Cheong et al.

(10) Patent No.: US 8,444,963 B2
(45) Date of Patent: May 21, 2013

(54) TUMOR SPECIFIC DELIVERY OF THERAPEUTIC AGENTS VIA LIPOSOMASE

(75) Inventors: Ian Cheong, Baltimore, MD (US); Shibin Zhou, Baltimore, MD (US); Kenneth W. Kinzler, Bel Air, MD (US); Bert Vogelstein, Baltimore, MD (US)

(73) Assignee: John Hopkins University, Baltimore, MD (US)

( * ) Notice: Subject to any disclaimer, the term of this patent is extended or adjusted under 35 U.S.C. 154(b) by 711 days.

(21) Appl. No.: 12/304,178

(22) PCT Filed: Jun. 19, 2007

(86) PCT No.: PCT/US2007/014274
§ 371 (c)(1), (2), (4) Date: Aug. 20, 2009

(87) PCT Pub. No.: WO2007/149433
PCT Pub. Date: Dec. 27, 2007

(65) Prior Publication Data

US 2011/0250258 A1 Oct. 13, 2011

Related U.S. Application Data

(60) Provisional application No. 60/814,546, filed on Jun. 19, 2006.

(51) Int. Cl.
*A01N 63/00* (2006.01)
*A01N 63/02* (2006.01)
*A61K 38/43* (2006.01)

(52) U.S. Cl.
USPC ....................... 424/93.2; 424/93.41; 424/94.3

(58) Field of Classification Search
None
See application file for complete search history.

(56) References Cited

FOREIGN PATENT DOCUMENTS

| | | |
|---|---|---|
| JP | 05-H501264 | 3/1993 |
| JP | 2005-298486 | 10/2005 |
| WO | 2005/037862 | 4/2005 |
| WO | 2006/046080 | 5/2006 |

OTHER PUBLICATIONS

Dang et al (Proc. National Acad. Sci. U.S.A, 98, p. 15155-15160).*
Dang (PNAS, vol. 98, No. 26, Dec. 18, 2001).*
Maurer et al (Expert Opinion Biol. Ther, 1(5), 2001).*
Messerer et al (Clinical Cancer Research, vol. 10, 6638-6649, Oct. 1, 2004).*
Dang et al (PNAS, 98:15155-15160, 2001).*
Mellaert et al., *Clostridium* spores as anti-tumour, Trends in Microbiology, vol. 14, No. 4, Apr. 2006, pp. 190-196.
Thurston et al., Cationic Liposomes Target Angiogenic Endthelial Cells in Tumors and Chronic Inflammation in Mice, J. Clin. Invest., vol. 101, No. 7, Apr. 1998, p. 1401-1413.
Diaz et al., Pharmacologic and Toxicologic Evaluation of C. noyi-NT Spores, Toxicological Sciences, 2005, vol. 88, No. 2, p. 562-575.
Van, M.E. et al, “Clostridium spores as anti-tumour agents,” Trends Microbiol, Apr. 2006, vol. 14, No. 4, p. 190-196.
Uziely, B. et al, “Liposomal Doxorubicin: Antitumor Activity and Unique Toxicities During Two Complementary Phase I Studies,” Journal of Clinical Oncology, Jul. 1, 1995, vol. 13, No. 7, p. 1777-1785.
[Online], Oct. 10, 2004, P1-14, http://web.archive.org/web/20041009180801/www.doxil.com/05_shared_pages/01_prescribing_info.html.
ten Hagen, T.L.M. et al, “Pegylated Liposomal Tumor Necrosis Factor-alpha Results in Reduced Toxicity and Synergistic Antitumor Activity After Systemic Administration in Comination with Liposomal Doxorubivin (Doxil) in Soft Tissue Sarcoma-Bearing Rats,” International Journal of Cancer, Jan. 1, 2002, vol. 97, No. 1, p. 115-120.
Lyass, O. et al, “Phase I Study of Doxil-Cisplatin Combination Chemotherapy in Patients with Advanced Malignancies,” Clinical Cancer Research, Oct. 2001, vol. 7, No. 10, p. 6040-3046.
Burstein, H.J., et al, “Phase I study of Doxil and vinorelbine in metastatic breast cancer,” Annals of Oncology, Sep. 1999, vol. 10, No. 9, p. 1113-1116.
Office Action issued in related Japanese Application No. 2009-516542, dated Nov. 8, 2012.

* cited by examiner

*Primary Examiner* — Brian J Gangle
(74) *Attorney, Agent, or Firm* — Banner & Witcoff, Ltd

(57) ABSTRACT

*Clostridium novyi* is an obligate anaerobe that can infect hypoxic regions within experimental tumors. We found that mice bearing large, established tumors were often cured when treated with *C. novyi* plus a single dose of liposomal doxorubicin. The secreted factor responsible for this phenomenon was identified and, surprisingly, proved to be a member of the lipase family. The gene encoding this protein, called liposomase, has the potential to be incorporated into diverse therapeutic methods to deliver specifically a variety of chemotherapeutic agents to tumors.

51 Claims, 6 Drawing Sheets

SEQUENCE LISTING

```
<160> NUMBER OF SEQ ID NOS: 6

<210> SEQ ID NO 1
<211> LENGTH: 443
<212> TYPE: PRT
<213> ORGANISM: Clostridium novyi

<400> SEQUENCE: 1

Met Gln Ser Lys Leu Lys Lys Phe Ile Ser Thr Ile Ser Val Ser Leu
 1               5                  10                  15

Phe Thr Leu Ala Ser Val Leu Thr Phe Ser Met Ala Lys Pro Val Asn
            20                  25                  30

Ala Phe Ala Lys Glu Asn Gln Lys Val Ser Gln Asn Asn Tyr Pro Ile
        35                  40                  45

Ile Leu Cys His Gly Cys Asn Gly Trp Gly Arg Thr Glu Asn Phe Gly
    50                  55                  60

Thr Val Ala Phe Gly Ala Arg Tyr Tyr Trp Gly Gly Asn Val Asp Leu
65                  70                  75                  80

Gln Gln Lys Leu Ile Glu Asn Gly Phe Thr Thr Tyr Thr Ala Ala Val
                85                  90                  95

Gly Pro Leu Ser Ser Asn Trp Asp Arg Ala Cys Glu Leu Tyr Ala Gln
            100                 105                 110

Ile Lys Gly Gly Arg Val Asp Tyr Gly Glu Ala His Ala Lys Lys His
        115                 120                 125

Gly His Ser Arg Tyr Gly Arg Tyr Tyr Arg Gly Phe Tyr Pro Glu Trp
    130                 135                 140

Gly Thr Lys Asp Glu Asn Gly Asn Ile Arg Lys Val His Leu Ile Gly
145                 150                 155                 160

His Ser Gln Gly Gly Gln Thr Ile Arg Met Leu Thr Thr Leu Leu Gly
                165                 170                 175

Gln Gly Lys Gln Glu Glu Ile Ser Ala Thr Gly Glu Asn Thr Asn Glu
            180                 185                 190

Leu Phe Lys Gly Gly His Asp Trp Val Ser Gly Leu Ile Thr Leu Ala
        195                 200                 205

Ser Pro His Asp Gly Thr Thr Leu Ala Asp Met Lys Gly Thr Asp Ala
    210                 215                 220

Ala Ala Ala Ile Gly Ile Gly Ala Val Gly Ser Met Leu Gly Asn Ile
225                 230                 235                 240

Ser Asn Ser Asp Ile Ile Phe Asp Leu Lys Val Asp Gln Trp Gly Leu
                245                 250                 255

Lys Arg Lys Pro Ser Glu Ser Phe Ile Ser Tyr Phe Asn Arg Cys Ala
            260                 265                 270

Thr Ser Lys Met Trp Asn Ser Lys Asp Ile Cys Ser Val Asp Leu Ser
        275                 280                 285

Thr Asn Gly Ala Val Glu Gln Asn Lys Trp Val Lys Ala Gln Pro Asn
```

-continued

```
    290                 295                 300

Val Tyr Tyr Phe Ser Trp Ala Cys Cys Gly Thr Ile Arg Asn Pro Ile
305                 310                 315                 320

Ser Ile Phe Gly His His Met Ala Ser Pro Ile Arg Met Ser Asp Lys
                325                 330                 335

Gly Leu Tyr Asn Val Gln Trp Ala Leu Gln Ala Gln Leu Met Gly Thr
            340                 345                 350

Tyr Ser Arg Asn Asn Pro Arg Arg Ala Ile Pro Val Ile Asp Ser Lys
        355                 360                 365

Trp Trp Pro Asn Asp Gly Tyr Val Asn Thr Ile Ser Glu Asn Gly Pro
    370                 375                 380

Lys Ala Gly Ser Thr Asp Glu Ile Val Asn Tyr Asn Gly Thr Pro Gln
385                 390                 395                 400

Ile Gly Lys Trp Asn Phe Met Gly Val Lys Asp Met Asp His Glu Asp
                405                 410                 415

Ile Ile Gly Arg His Trp Asn Gly Ala Pro Asn Phe Phe Ile Asp Met
            420                 425                 430

Ala Gln Met Leu Arg Asn Leu Pro Val Thr Glu
        435                 440


<210> SEQ ID NO 2
<211> LENGTH: 1332
<212> TYPE: DNA
<213> ORGANISM: Clostridium novyi

<400> SEQUENCE: 2

atgcaatcga agcttaaaaa atttatttca acaatctctg tatctttatt tactttagct      60

tctgtgttaa cgttttcaat ggcgaagccg gtgaatgcat ttgctaaaga aaatcaaaaa     120

gtatcacaaa ataattatcc tataatactt tgtcatggat gtaatggatg gggtagaact     180

gaaaacttcg gaacagttgc ttttggagca agatattact ggggtggaaa tgttgactta     240

caacaaaagc ttattgaaaa tggatttaca acttatacag cagctgtagg accactttcg     300

agtaactggg acagagcttg tgaactttat gctcaaatta aaggtggaag ggttgactat     360

ggtgaagctc atgctaaaaa acatggacac tctagatatg gaagatatta cagaggtttt     420

tatccagaat ggggaacaaa ggatgaaaac ggcaatatac gtaaagttca tttaatagga     480

cacagccaag gtggacaaac tatacgtatg ttaactactc ttcttggtca aggtaaacaa     540

gaagaaatat cagcaacagg agaaaatact aacgaattat ttaaaggtgg acatgattgg     600

gtttcaggac taataacatt agcatcacca catgacggaa ctactttagc tgatatgaaa     660

ggtacagatg ctgcagcagc aattggtata ggtgcagtgg gatcaatgct aggaaatata     720

tctaattcag atataatatt tgatttaaag gttgatcaat ggggacttaa gagaaaacct     780

tcagaatcat ttataagcta ttttaataga tgtgctacaa gtaaaatgtg gaactcaaaa     840

gatatttgtt cagtagattt aagtaccaat ggtgctgtag aacaaaacaa atgggtaaag     900

gcccaaccaa atgtatacta cttctcatgg gcatgttgtg gaactataag aaatccaatt     960

agcatatttg gacatcatat ggcaagtcct ataagaatga gtgacaaggg actatataat    1020

gttcaatggg cattacaagc tcaattaatg ggaacatata gcagaaataa tcctcgtcgt    1080

gcaatacctg taattgatag taaatggtgg ccaaatgatg gatatgtaaa tactatttct    1140

gaaaatggac ctaaagctgg atcaactgat gaaattgtaa attataatgg aacacctcaa    1200

ataggtaaat ggaactttat gggtgttaaa gacatggatc acgaagatat aataggaaga    1260

cactggaatg gagcacctaa cttctttata gacatggctc aaatgcttag aaatcttcct    1320
```

-continued

```
gtaactgaat aa                                                          1332


<210> SEQ ID NO 3
<211> LENGTH: 73
<212> TYPE: DNA
<213> ORGANISM: Clostridium novyi

<400> SEQUENCE: 3

tgcaccacca ccaccaccac aaagaaaatc aaaaagtatc acaaaataat tatcctataa      60

tactttgtca tgg                                                         73


<210> SEQ ID NO 4
<211> LENGTH: 49
<212> TYPE: DNA
<213> ORGANISM: Clostridium novyi

<400> SEQUENCE: 4

ctgaccggtt tattattcag ttacaggaag atttctaagc atttgagcc                  49


<210> SEQ ID NO 5
<211> LENGTH: 45
<212> TYPE: DNA
<213> ORGANISM: Clostridium novyi

<400> SEQUENCE: 5

gtaaagttca tttaatagga cacggtcaag gtggacaaac tatac                      45


<210> SEQ ID NO 6
<211> LENGTH: 45
<212> TYPE: DNA
<213> ORGANISM: Clostridium novyi

<400> SEQUENCE: 6

gtaaagttca tttaatagga cactaataag gtggacaaac tatac                      45
```

TUMOR SPECIFIC DELIVERY OF THERAPEUTIC AGENTS VIA LIPOSOMASE

This application claims the benefit of U.S. provisional application Ser. No. 60/814,546 filed Jun. 19, 2007, the disclosure of which is expressly incorporated herein.

The U.S. Government retains certain rights in the invention according to the provisions of a grant from the NIH, CA 62924.

TECHNICAL FIELD OF THE INVENTION

This invention is related to the area of oncology. In particular, it relates to treatment of tumors which enhance the selective toxicity of anti-cancer agents.

BACKGROUND OF THE INVENTION

There is no dearth of drugs that can kill cancer cells. The challenge is achieving specificity, i.e., killing the cancer cells while sparing the normal cells. There are three basic strategies now used to accomplish this specificity. One (selective toxicity) employs drugs that have more potent growth-inhibitory effects on tumor cells than on normal cells (1, 2) This strategy underlies the success of conventional chemotherapeutic agents as well as those of newer targeted therapies such as imatinib. The second strategy (delivery) employs agents such as antibodies or genes that specifically react with tumor cells or are predominantly expressed within tumor cells, respectively (3, 4). The third strategy (angiogenic) exploits abnormal aspects of tumor vasculature with agents such as Avastin (5, 6) or drugs incorporated into liposomes (7). Liposomes are relatively large particles that can penetrate through the fenestrated endothelium present in tumors and a few other organs (8, 9). Once they gain access to tumors, they persist and eventually release their contents and raise local drug concentrations through the enhanced permeabilization and retention (EPR) effect (10). Though each of these strategies has proven merit, the therapeutic results achieved are usually less than desired. The problems arise, in part, because the achieved specificity with any one of them is imperfect, limiting the amount of drug that can be safely administered without causing systemic toxicity.

There is a continuing need in the art to develop treatments for cancers that are more effective and less toxic.

SUMMARY OF THE INVENTION

According to one embodiment of the invention a composition is provided, useful for delivering therapeutic agents. The composition comprises toxin-defective *Clostridium novyi* spores; and a liposome comprising an anti-tumor drug or biological agent.

According to another embodiment of the invention another composition is provided. The composition comprises a toxin-defective *Clostridium novyi* liposomase according to SEQ ID NO: 1 or according to SEQ ID NO: 1 with a substitution mutation in the GXSXG lipase motif (residues 160-164 of SEQ ID NO: 1) and a liposome comprising an anti-tumor drug or biological agent.

Another aspect of the invention is a kit. The kit comprises a toxin-defective *Clostridium novyi* liposomase according to SEQ ID NO: 1 or according to SEQ ID NO: 1 with a substitution mutation in the GXSXG lipase motif; and a liposome comprising an anti-tumor drug or biological agent.

Still another aspect of the invention is a kit. The kit comprises toxin-defective *Clostridium novyi* spores; and a liposome comprising an anti-tumor drug or biological agent.

Yet another embodiment of the invention is a method of treating a cancer patient. A first agent which is toxin-defective *Clostridium novyi* spores and a second agent which is a liposome comprising an anti-tumor drug or biological agent are administered to the cancer patient. The tumor thereby regresses or its growth is slowed or arrested.

An additional aspect of the invention is a method of treating a cancer patient in which a first agent and a second agent are administered to the cancer patient. The first agent is a toxin-defective *Clostridium novyi* liposomase according to SEQ ID NO: 1 or according to SEQ ID NO: 1 with a substitution mutation in the GXSXG lipase motif, and the second agent is a liposome comprising an anti-tumor drug or biological agent. The tumor thereby regresses or its growth is slowed or arrested.

Also provided by the present invention is a method of treating a cancer patient in which a first and a second agent are administered to the cancer patient. The first agent is a vector encoding toxin-defective *Clostridium novyi* liposomase according to SEQ ID NO: 1 or according to SEQ ID NO: 1 with a substitution mutation in the GXSXG lipase motif, and a second agent is a liposome comprising an anti-tumor drug or biological agent. The tumor thereby regresses or its growth is slowed or arrested.

The present invention also provides a composition comprising an isolated and purified toxin-defective *Clostridium novyi* liposomase protein according to SEQ ID NO: 1 or according to SEQ ID NO: 1 with a substitution mutation in the GXSXG lipase motif.

The invention further provides a conjugate protein comprising a toxin-defective *Clostridium novyi* liposomase protein according to SEQ ID NO: 1 or according to SEQ ID NO: 1 with a substitution mutation in the GXSXG lipase motif; and a polypeptide ligand which binds to a receptor on a tumor cell. A polynucleotide which encodes the conjugate protein is also provided.

The invention still further provides a composition comprising an isolated and purified polynucleotide encoding a toxin-defective *Clostridium novyi* liposomase protein according to SEQ ID NO: 1 or according to SEQ ID NO: 1 with a substitution mutation in the GXSXG lipase motif.

These and other embodiments which will be apparent to those of skill in the art upon reading the specification provide the art with a set of tools for treating cancers that can have widespread applicability across a range of tumors and a range of therapeutic agents.

BRIEF DESCRIPTION OF THE DRAWINGS

FIGS. 1A and 1B show effect on CT26 tumors. FIGS. 1C and 1D show effect on HT116 tumors. FIGS. 1A and 1C show tumor volume and FIGS. 1B and 1D show percent survival.

(FIG. 2A) At 0 hours, Doxil was administered to athymic nude mice bearing tumors of ~300

$mm^3$ in size. Another group of mice was intravenously injected with *C. novyi*-NT spores 16 hours prior to Doxil. Mice were sacrificed at the indicated time points and doxorubicin extracted from tissues and measured by fluorometry. Means and standard deviations from three mice per time point are shown. (FIG. 2B) Tumors were snap-frozen 16 hr after injection with Doxil and cryostat sections from the central regions examined using a fluorescence microscope. The fluorescence signal from doxorubicin in liposomes is quenched (see Supplementary Materials and Methods), while released doxorubicin emits fluorescence at 590 nm. Colocalization of the doxorubicin fluorescence and nuclear DNA, stained with DAPI, is observed in the tumors treated with *C. novyi*-NT spores.

(FIG. 3A) *C. novyi*-NT was grown in medium until late log phase and the medium cleared of cells through centrifugation. Following precipitation with 40% saturated ammonium sulfate, ion exchange chromatography was performed and fractions evaluated for liposome-disrupting activity. (FIG. 3B) The peak fractions (30-31) from (FIG. 3A) were pooled and fractionated by gel filtration chromatography. (FIG. 3C) The peak fractions (29-30) from (FIG. 3B) were fractionated by SDS-polyacrylamide gel electrophoresis.

FIG. 4A-4D. Functional analysis of liposomase. Plasmids carrying the wt or mutant forms of the NT01CX2047 gene were introduced into *E. coli*. "Cured" bacteria represent those originally containing the wt gene and grown in the absence of selective antibiotics until the plasmid was lost. Cellular lysates from three independent clones of each bacterial strain were generated after induction of expression by IPTG and used for the following: (FIG. 4A) Western blotting with an antibody to oligohistidine confirmed the presence of similar amounts of wt and mutant proteins in the bacteria. (FIG. 4B) Lipase activity was analyzed using the fluorescent lipase substrate, 1,2-dioleoyl-3-pyrenedecanoyl-rac-glycerol. (FIG. 4C) Liposome-disrupting activity was assessed using Doxil. (FIG. 4D) Liposome-disrupting activity of lipases purified from ten different organisms were assessed using Doxil. Means and standard deviations of data from at least two independent experiments are shown in (FIG. 4B) to (FIG. 4D).

(FIG. 6A) Time course of doxorubicin release from Doxil in the presence of growth medium from *C. novyi*-NT cultures ("conditioned medium"). *C. novyi*-NT was grown until late log phase and the medium cleared of cells via centrifugation. Significant liposome-disrupting activity was noted (red symbols) while no increase in fluorescence was observed in the indicated controls. (FIG. 6B) Liposome-disrupting activity as a function of growth time in culture. *C. novyi*-NT spores were inoculated in growth medium and harvested at various times thereafter. Following clearance of bacterial cells, liposome-disrupting activity was measured in the supernatant and correlated with absorbance at 600 nm. Means and standard deviations of data from at least two independent assays of liposome-disrupting activity are shown. Standard deviations are not visible when the bars representing them are smaller than the symbol of the corresponding data point.

DETAILED DESCRIPTION OF THE INVENTION

Figures 1A, 1B, 1C, 1D:
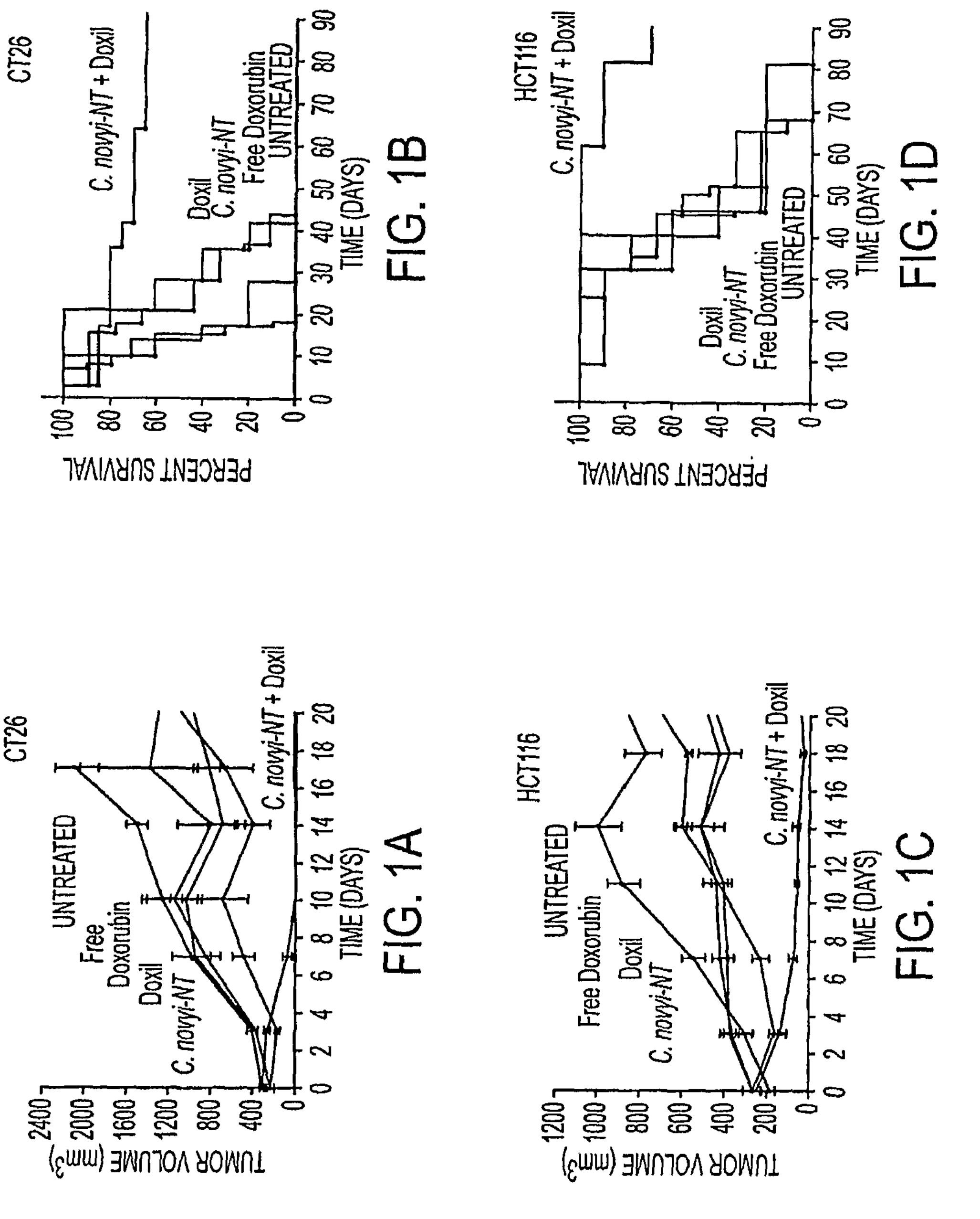
FIG. 1A-1D. Effects of treatment with *C. novyi*-NT plus Doxil. Mice bearing the indicated tumors were treated on day 0 with various combinations of the indicated agents. Free doxorubicin plus *C. novyi*-NT spores resulted in deaths of all animals within two weeks and is not shown. Means and standard errors of data collected from at least five mice per group are illustrated. The differences between *C. novyi*-NT plus Doxil and the other groups were significant ($p<0.0006$, log-rank test).

The inventors have developed methods for treating tumors. The methods enhance the tumor specificity of treatments, thereby reducing systemic toxicities. Using a combination of a protein made by *C. novyi*-NT and liposome encapsulated drugs or biological agents, the efficacy of tumor elimination is greatly increased. The protein, while having lipase enzymatic activity appears to function non-enzymatically as a liposome disrupter. The lipase enzyme activity is not necessary for the liposome disrupting activity. Thus both wild-type and lipase-negative mutants can be used for this function. Moreover, the lipsome-disrupting function can be delivered by the protein as elaborated in situ by live *C. novyi*-NT, or by a cell-free preparation of the protein itself. Furthermore, the protein can be delivered as part of a conjugate or fusion protein which provides additional desirable functionality to the liposomase protein.

One of the potential advantages of the approach described here is that it is generally applicable to any chemotherapeutic drug or biological agent that can be encapsulated in a liposome. These include drugs of the following categories as examples: topoisomerase inhibitors, DNA synthesis inhibitors, cell division inhibitors, angiogenesis inhibitors, and microtubule inhibitors. Antibodies and antibody conjugates, such as rituxan, herceptin and erbitux, can also be encapsulated in a liposome. Further, cytokines and other bioactive proteins which may enhance the patient's endogenous tumor-fighting systems may be used. Such cytokines can include, without limitation: IL-2 and interferon-alfa 2b and GM-CSF. Particular drugs, cytokines, and antibodies which can be used without limitation include: abarelix; aldesleukin; Alemtuzumab; alitretinoin; allopurinol; altretamine; amifostine; anakinra; anastrozole; arsenic trioxide; asparaginase; azacitidine; BCG Live; bevacizumab; bexarotene capsules; bexarotene gel; bleomycin; bortezombi; bortezomib; busulfan; calusterone; capecitabine; carboplatin; carmustine; celecoxib; cetuximab; chlorambucil; cisplatin; cladribine; clofarabine; cyclophosphamide; cytarabine; dacarbazine; dactinomycin, actinomycin D; dalteparin sodium; darbepoetin alfa; dasatinib; daunorubicin; daunomycin; decitabine; denileukin; Denileukin diftitox; dexrazoxane; dexrazoxane; docetaxel; doxorubicin; dromostanolone propionate; eculizumab; Elliott's B Solution; epirubicin; epirubicin hcl; epoetin alfa; erlotinib; erlotinib; estramustine; etoposide phosphate; etoposide, VP-16; exemestane; fentanyl citrate; Filgrastim; floxuridine; fludarabine; fluorouracil, 5-FU; fulvestrant; gefitinib; gemcitabine; gemcitabine hcl; gemicitabine; gemtuzumab ozogamicin; goserelin acetate; histrelin acetate; hydroxyurea; Ibritumomab Tiuxetan; idarubicin; ifosfamide; imatinib mesylate; Interferon alfa-2a; Interferon alfa-2b; irinotecan; lapatinib ditosylate; lenalidomide; letrozole; leucovorin; leucovorin; leucovorin; leucovorin; Leuprolide Acetate; levamisole; lomustine, CCNU; meclorethamine, nitrogen mustard; megestrol acetate; melphalan, L-PAM; mercaptopurine, 6-MP; mesna; methotrexate; methoxsalen; mitomycin C; mitotane; mitoxantrone; nandrolone phenpropionate; nelarabine; Nofetumomab; Oprelvekin; oprelvekin; oxaliplatin; paclitaxel; paclitaxel protein-bound particles; palifermin; pamidronate; panitumumab; pegademase; pegaspargase; Pegfilgrastim; Peginterferon alfa-2b; pemetrexed disodium; pentostatin; pipobroman; plicamycin, mithramycin; porfimer sodium; procarbazine; quinacrine; Rasburicase; Rituximab; sargramostim; sorafenib; streptozocin; sunitinib; sunitinib maleate; talc; tamoxifen; temozolomide; teniposide, VM-26; testolactone; thalidomide; thioguanine, 6-TG; thiotepa; topotecan; topotecan hcl; toremifene;

Tositumomab; Tositumomab/I-131 tositumomab; trastuzumab; tretinoin, ATRA; Uracil Mustard; valrubicin; vinblastine; vincristine; vinorelbine; vorinostat; zoledronate; and zoledronic acid.

The gene encoding the liposomase has a sequence as shown in accession no. CP000382 of GenBank (SEQ ID NO: 2). The protein has a sequence as shown in accession no. ABK60711 (SEQ ID NO: 1). The first 35 amino acids are predicted to be cleaved as a signal sequence. Mutants having amino acid substitutions in the highly-conserved GXSXG lipase motif (residues 160-164 of SEQ ID NO: 1) also retain liposomase activity and can be used. For example, the S127G mutant (mutation at serine 162 in SEQ ID NO: 1) can be used to provide liposomase activity. Other lipase-defective mutants can be used as well. Other substitutions of Serine-127 (residue 162 in SEQ ID NO: 1) can be with amino acids A, C, D, E, F, G, H, I, K, L, M, N, P, Q, R, T, V, W, or Y.

Compositions according to the invention can be made before or after administration to a human or other mammal. Thus, components of the compositions can be administered separately or mixed. If separately, the components can be administered in any order. The components may form the composition when they are within a patient or other mammal. The components of the compositions can be packaged together or separately in a kit. Thus multiple vessels or containers within a single package may be provided to an end-user. The end user may administer the components separately or mixed, at one time or at more then one time.

Kits comprising the useful components for practicing the anti-tumor methods of the present invention can be packaged in a divided or undivided container, such as a carton, bottle, ampule, tube, etc. The spores, liposomase, and anti-tumor agents can be packaged in, e.g., dried, lyophilized, or liquid form. Additional components provided can include vehicles for reconsititution of dried components. Preferably all such vehicles are sterile and apyrogenic so that they are suitable for injection into a mammal without causing adverse reactions. The anti-tumor agents other than the spores are also preferably sterile. The spores are preferably microbiologically pure, i.e., containing no other bacteria other than the desired spore-forming anaerobe.

Methods for making liposomes are well known in the art. See for example, Mozafari, Cell Mol Biol Lett. 2005; 10(4): 711-9; Andresen et al., Prog Lipid Res. 2005 January; 44(1): 68-97; Jensen et al., Mol Cancer Ther. 2004 November; 3(11):1451-8; Pupo et al., J Control Release. 2005 May 18; 104(2):379-96p; Brandl, Biotechnol Annu Rev. 2001; 7:59-85. Any technique known in the art for making liposomes may be used.

*C. novyi* spores can be prepared as is known in the art. Preferably the spores will be from a toxin-defective strain. See for example, U.S. Patent Application 20050079157, the contents of which are expressly incorporated herein. Toxin can be eliminated by a process of curing of a bacteriophage or plasmid. A *C. novyi* useful as a starting material (ATCC 19402) can be obtained from the American Type Culture Collection, 10801 University Boulevard, Manassas, Va., 20110-2209.

While strains need not be totally non-toxigenic, it is desirable that at least one of the toxin genes be mutated, deleted, or otherwise inactivated to render the bacteria less harmful to the host. If a toxin gene is episomal or on a phage, then curing of the episome or phage can be used to eliminate the toxin gene. Techniques are well known in the art for mutagenesis and screening of mutants and for curing episomes.

Isolated and bacteriologically pure vegetative bacteria or spores, according to the invention are those which are not contaminated with other bacteria or spores. Microbiological techniques for obtaining such pure cultures are will known in the art. Typically single colonies are picked and spread upon an agar nutrient medium, separating colonies so that new colonies arise that are the progeny of single cells. This process is typically repeated to ensure pure cultures. Alternatively, liquid cultures can be serially diluted and plated for single colony formation. Serial repetition is desirable to ensure colony formation from single cells. See, e.g., J. H. Miller, Experiments in Molecular Genetics, Cold Spring Harbor Laboratory, NY, 1972.

Spores, liposomase, liposomase conjugates, and nucleic acids encoding liposomase or fusion proteins of it, can be administered to a tumor-bearing mammal by any means which will afford access to the tumor. Spores can be injected intravenously, intradermally, subcutaneously, intramuscularly, intraperitoneally, intratrumorally, intrathecally, surgically, etc. Preferred techniques are intravenous and intratumoral injections. Tumor bearing mammals can be, for example, humans, pets, such as dogs and cats, agricultural animals such as cows, sheep, goats and pigs, and laboratory animals, such as rats, hamsters, monkeys, mice, and rabbits.

The present delivery system is useful for protein therapy or gene therapy or a combination thereof. Thus the liposomase can be provided as a protein or as a polynucleotide encoding lipsomase. Similarly, the anti-tumor drug or biological agent may be a protein or a polynucleotide, as well as a small chemical entity, for example, not a biological polymer. Polynucleotides can be provided in a viral or non-viral vector. Any vectors which are known in the art can be used, without limitation. The vector constructs may contain a tumor-specific promoter to enhance the specificity of the treatment. Examples of such promoters are known in the art. CXCR4 promoter is tumor-specific in melanomas; Hexokinase type II promoter is tumor-specific in lung cancer; TRPM4 (Transient Receptor Potential-Melastatin 4) promoter is preferentially active in prostate cancer. The anti-tumor drug may be one that directly or indirectly affects the tumor. Thus, for example, it can be a protein which stimulates the native immune response to the tumor. Alternatively, it can be an antibody which mobilizes other immune system components to destroy tumor cells. Still other agents may be toxic to tumor cells. The choice of agent is well within the skill of the artisan.

Conjugate proteins are post-translationally linked proteins; they may be linked by chemical linking of two polypeptides, directly or through an intermediate. Alternatively, the proteins may be linked via co-translation of two coding regions within a single open reading frame. Any means for joining two polypeptides that are not linked in nature may be used. One type of conjugate which can be used utilizes an antibody molecule or portion thereof as a second protein. Thus, as an example, liposomase can be linked to a variable region of an antibody thus providing the liposomase with a means of targeting to a particular site in the body which expresses the antigen to which the antibody binds. Linkers may be used between portions of the conjugate proteins as desired.

Isolated and purified liposomase protein according to the invention is a preparation in which the liposomase activity comprises at least 10%, 25%, 40%, 55%, 70%, 85%, or 95% of the protein in a composition. Isolated and purified liposomase-encoding polynucleotide is one which is separated from other genes of the *C. novyi* genome. Thus it is separated from the genome-adjacent sequences encoding hypothetical proteins NT01CX_2046 and NT01CX_2048. The complete genome of *C. novyi*-NT has been determined and is available at NCBI as NC_008593. It is a circular DNA of 2,5478,720 nt.

The methods and compositions of the present invention can be applied to any tumor type. The principles upon which the invention relies (such as the selective ability of liposomes to penetrate through the fenestrated endothelium present in tumors and a few other organs (8, 9), and the enhanced release of contents from a liposome in the presence of liposomase,) apply to any tumor. Thus the present invention can be used to treat tumors of the gastrointestinal tract, such as stomach, intestine, colon, rectum, esophagus, tumors of the kidney, breast, lung, liver, head and neck, and brain.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Cell Lines. HCT116 (CCL-247, human colorectal carcinoma) and CT26 (CRL-2638, murine colorectal adenocarcinoma) were purchased from the American Type Culture Collection. Both lines were grown in McCoy's 5A Medium (Invitrogen) supplemented with 5% FBS (Hyclone) at 37° C. in 5% $CO_2$ Reagents. Doxorubicin was purchased from Bedford Laboratories, Bedford, Ohio. PEGylated liposomal doxorubicin (DOXIL®) was purchased from Tibotec Therapeutics, Raritan, N.J. Chicken Egg L-α-Phosphatidylcholine (EPC), Hydrogenated Chicken Egg L-α- Phosphatidylcholine (HEPC), 1,2-Distearoyl-sn-Glycero-3-Phosphoethanolamine-N-[Methoxy(Polyethylene glycol)-2000] (DSPE-$PEG_{2000}$) and Cholesterol (Chol) were purchased from Avanti Polar Lipids, Alabaster, Ala. Irinotecan HCl (CAMPTOSAR™) was purchased from Pharmacia & Upjohn Co., Kalamazoo, Mich. Calcimycin A23187 and Triolein were obtained from Sigma (St. Louis, Mo.). 1,2-dioleoyl-3-pyrenedecanoyl-rac-glycerol (DPG) was obtained from MarkerGene Technologies (Eugene, Oreg.). A set of nine purified lipases were purchased from Fluka, Switzerland. *C. novyi*-NT spores were prepared as previously described (1).

Preparation of Liposomes. A mixture of HEPC:Chol: DSPE-$PEG_{2000}$ at a molar ratio of 50:45:5 was solubilized in chloroform and dried to a thin film under rotary evaporation then further dried under vacuum for 2 hours. The film was hydrated with 300 mM $MnSO_4$ and submerged in a 65° C. sonication bath Bransonic, Danbury, Conn.) to form Large Multilamellar Vesicles (MLVs). This lipid suspension was extruded 10 times through a double stack of 0.1 um Nuclepore filters (Whatman, Florham Park, N.J.) using a Lipex Thermobarrel Extruder (Northern Lipids, Vancouver, BC, Canada). The resulting colloidal suspension of Single Unilamellar. Vesicles (SUV) was filter-sterilized then dialysed against 300 mM sucrose at 4° C. to exchange the external milieu of the liposomes. The mean size of the SUVs was 100.2 nm (polydispersity index=0.129) as determined by quasi-elastic light scattering using a Malvern Zetasizer 3000 (Malvern, Worcestershire, UK), Liposomal CPT-11. CPT-11 was actively loaded into liposomes using a $MnSO_4$ pH gradient loading method (2-4). Irinotecan was mixed with liposomes at a drug:lipid molar ratio of 1:3 and incubated at 65° C. for 10 mM. Calcimycin was then added at a ratio of 1 μg Calcimycin:10 mmol lipids and the suspension incubated at 65° C. for 45 min. The drug-loaded liposomes were then filter-sterilized and dialyzed against 300 mM sucrose at 4° C. to remove unencapsulated CPT-11. Dialysis was performed in the dark to minimize photo-degradation of the drug. Encapsulation efficiency was typically >99% as determined by disruption of liposomes with 1-butanol and fluorometric measurement (excitation at 390 nm, emission at 460 nm) using a fluorescence plate reader (Fluostar Galaxy, BMG LabTech, GmbH). Concentrations were derived by reference to a CPT-11 standard curve.

Animal models. All animal experiments were overseen and approved by the Animal Welfare Committee of Johns Hopkins University and were in compliance with University standards. Six- to 8-week old mice purchased from Harlan Breeders, IN, were used for tumor implantation studies. Balb/c mice were used to establish CT26 tumors and athymic nu/nu mice were used to establish HCT116 xenografts. A minimum of five animals were used for each experimental arm. Five million tumor cells were injected subcutaneously into the right flank of each mouse and allowed to grow for ~10 days before randomization and treatment. *C. novyi*-NT spores were administered as a bolus tail vein injection of 300 million spores suspended in 0.2 ml phosphate buffered saline. Free and liposomal drugs in the relevant arms were administered 16 hours later via the same route. The doses of Doxil, doxorubicin, liposomal irinotecan and irinotecan were 10 mg/kg and 25 mg/kg, respectively. Tumor volume was calculated as length×width$^2$×0.5.

Pharmacokinetic Study. HCT116 xenografts were established in athymic nu/nu mice and treated as described above. Tissue samples were harvested at various times after treatment, suspended in 70% ethanol, 0.3 N HCl and homogenized (Ultra-Turrax® T25 Basic, IKA, NC) to extract doxorubicin. Following centrifugation, doxorubicin fluorescence (excitation at 470 nm, emission at 590 nm) in the supernatant was measured with a fluorescence plate reader (FLUOSTAR GALAXY™, BMG LabTech, GmbH). Concentrations were derived by reference to a doxorubicin standard curve.

Liposome-Disruption Assay. Samples were mixed with DOXIL™ liposomal doxorubicin (100 μl sample+5 μl DOXIL™ liposomal doxorubicin in a 96-well plate or 50 μl sample+2 μl DOXIL™ in a 384-well plate). Increase in fluorescence caused by the dequenching of released doxorubicin was kinetically measured over 30-60 minutes using excitation at 470 nm and emission at 590 nm (5). All measurements were performed at 37° C. in a fluorescence plate reader. A typical readout is shown in FIG. S1. Liposome-disrupting activity was defined as the maximum slope of the release curve.

Biochemical Purification. *C. novyi*-NT spores were inoculated into 20 ml Bagadi Medium (6) and incubated in an anaerobic chamber (Type A, Coy Labs, Grass Lake, Mich.) at 37° C. for ~16 hr. One ml of this starter culture was used to inoculate 100 ml Bagadi Medium that had been pre-equilibrated in the anaerobic chamber. This culture was grown to late log phase then centrifuged at 5,000 g to remove bacteria. The supernatant was precipitated with 50% saturated ammonium sulfate at 4° C. for 1 hour, then centrifuged at 5,000 g. After discarding the supernatant, the pellet was solubilized in TN buffer (100 mM Tris-HCl, pH 7.5, 0.1 M NaCl) and filter-sterilized. All subsequent chromatography was performed on an ÄKTA Purifier FPLC system (Amersham Biosciences, Piscataway, N.J.). The filtered sample was loaded onto a mono Q 5/50 GL (Amersham) column equilibrated in TN buffer. The proteins were eluted with a linear gradient of ten column volumes formed from TN buffer and 100 mM Tris-HCl 7.5, 1 M NaCl. The fractions collected were assayed for doxorubicin releasing activity as described above. The two most active fractions from the mono Q column were pooled and loaded onto a HiLoad 16/60 Superdex 200 (Amersham) column equilibrated in 100 mM Tris-HCl pH 7.5, 0.5 M NaCl. The column was isocratically eluted with the same buffer over 1.5 column volumes. The fractions were assayed for doxorubicin disrupting activity as described above. Proteins in the two most active fractions were separated by electrophoresis through an SDS-polyacrylamide gel and silver-stained using the SilverSNAP Stain Kit II (Pierce, Rockford, Ill.). The single dominant band (≈45 kD) was excised for analysis by LC/MS/MS.

LC/MS/MS Peptide Analysis. The excised protein band was digested in-gel with trypsin, and analyzed as previously described (7). In brief, purified tryptic fragments were injected onto a 150×0.3 mm Vydac reverse phase column at 10 μL/min for 5 min in 5% buffer B using an Agilent 1100 Series Capillary-LC system. Buffers A (0.1% acetic acid) and B (99.9% acetonitrile and 0.1% acetic acid) were employed in the liquid chromatography (LC) step of the LC/MS/MS analysis. Peptides were eluted from the column with a 10-65% buffer B gradient over 90 minutes at a rate of 2 μL/min. Eluted peptides were detected by a LCQ DECA XP mass spectrometer (Thermo, Mass.), equipped with an electrospray ionization source, a low flow metal needle assembly operating in data dependent mode. The method consisted of two scan events, a full scan and a second data dependent MS/MS scan. The dynamic mass range of the full scan was set at 300 to 3000 m/z. The resulting MS/MS data dependent scan rejected known 'contaminant' masses of 371.0, 391.0, 445.0, 462.0, 1221.89, 1321.9, 1421.9, 1521.8, 1521.9, 1621.9, 1721.9 and 1821.9 m/z. Other method settings included a default charge state set to 4, dynamic exclusion with repeat count set to 2, repeat duration 1 min, an exclusion list size of 25 and exclusion duration 3 min. All other method parameters were default values set by the Xcaliber software v.1.2 (Thermo, MA).

Cloning of oligohistidine-fusion proteins. The coding sequence of NT01CX2047, devoid of its N-terminal secretion signal (as predicted by SignalP 3.0) was PCR-amplified with Phusion Taq Polymerase (Finnzymes, Espoo, Finland) using forward primer 5'-TGCACCACCACCACCACCACAAAGAAAATCAAAAAGTATCACAAAATAAT TATCCTATAATACTTTGTCATGG (SEQ ID NO: 3) and reverse primer 5'-CTGACCGGTTTATTATTCAGTTACAGGAAGATTT CTAAGCATTTGAGCC (SEQ ID NO: 4). The $(CAC)_6$ sequence in the forward primer added six histidine residues at the N-terminus of the encoded protein. This PCR product was digested with Age I to create an insert with one sticky end. The cloning vector pCR2.1/T7-GFP (Invitrogen, Carlsbad, Calif.) was digested with Nde I, blunted with T4 DNA polymerase, then digested with Age I to create a single sticky end. The vector and insert were ligated to create pLip. The expected sequences of the inserts were verified by DNA sequencing.

Cloning of S127G and S127X variants. The pLip plasmid was digested with SnaB I to excise a 45 bp fragment containing the serine residue to be mutated. The pLip(S127G) plasmid was generated by blunt-end ligating the digested plasmid with a replacement 45 bp double-stranded oligonucleotide of sequence 5'-GTAAAGTTCATTTAATAGGACACGGTCAA GGTGGACAAACTATAC (SEQ ID NO: 5). The plasmid pLip(S127X) plasmid was generated in the same fashion using the double-stranded oligonucleotide 5'-GTAAAGTTCATTTAATAGGACA C TAATAAGGTGGACAAACTATAC (SEQ ID NO: 6). The targeted alterations (underlined above) and orientation of the inserts were verified by DNA sequencing.

Protein Expression. The expression vectors described above were transformed by heat shock into the Rosetta-gami (DE3)pLysS strain of *E. coli* (Novagen, Madison, Wis.). Three clones per expression construct were picked and each was cultured in 20 ml HyperBroth (AthenaES, Baltimore, Md.) under antibiotic selection (100 μg/ml ampicillin+34 μg/ml chloramphenicol) at room temperature. As a negative control, bacteria carrying the pLip plasmid were "cured" of their plasmid through growth in the absence of selective antibiotics. Loss of plasmid was verified by PCR. Expression was induced using IPTG for 1 hour, reaching an $OD_{600}$~0.2, after which the bacteria were pelleted by centrifugation and resuspended in 100 mM Tris-HCl, pH 7.5. Lysates were prepared by sonication in a Bioruptor sonicating bath (Diagenode, Belgium) and centrifugation at ~14,000 g was performed to remove insoluble matter. Western Blotting using an α-poly-Histidine mouse mAb (R&D Systems, MN) was used to confirm the presence of the expected proteins.

Lipase Assay. EPC:Triolein:DPG in a molar ratio of 2:5:1 were mixed in chloroform and dried to a thin lipid film under rotary evaporation, then dried further under high vacuum for 2 hours. The film was hydrated with 100 mM glycine buffer, pH 9.5, 19 mM sodium deoxycholate to yield a final DPG concentration of 1 mM. This suspension was vortexed vigorously to form an emulsion for use as a substrate. Samples were mixed with this substrate (30 μl sample+5 μl sample) in a 384-well plate). Increase in fluorescence caused by catalytic release of pyrenedecanoic acid was kinetically measured over 2 hours using excitation at 320 nm and emission at 405 nm. All measurements were performed at 37° C. in a FluoStar Galaxy fluorescence plate reader. Lipase Activity units were derived by reference to a *Pseudomonas cepacia* lipase standard curve. 1 unit (U) corresponds to the equivalent amount of *P. cepacia* lipase activity which liberates 1 μmol per minute of oleic acid from triolein.

Lipase Panel Experiment. Purified NT01CX2047 enzyme and nine other purified lipases were dissolved in 100 mM Tris-HCl, pH 7.5 to a concentration of 1 mg/ml. Fifty μl of Assay Buffer (100 mM Tris-HCl pH 7.5+0.125M NaCl) was pipetted into 384-well plates, followed by 2 μl of the relevant lipase and 1 μl of DOXIL. Samples were assayed in duplicate for liposome-disrupting activity as described above.

EXAMPLE 2

Spores Plus Liposomes In Vivo in First Model

We used syngeneic CT26 colorectal tumors in BALB/c mice. *C. novyi*-NT spores were injected intravenously, and once germination had begun in the tumors (~16 hr after injection) a single dose of Doxil, at 10 mg/kg, was administered through the tail vein. Doxil is a liposomal formulation which encapsulates doxorubicin, a DNA-damaging agent and widely used chemotherapeutic agent. Liposome-encapsulated doxorubicin has been shown to result in improved outcomes compared to unencapsulated doxorubicin in a variety of experimental and clinical studies (18-21). The liposomes in Doxil are surface modified by PEGylation to increase their circulation time (18). As previously documented (11, 12), treatment with *C. novyi*-NT spores alone resulted in germination and necrosis within the centrally hypoxic region of the tumor, but left a well-oxygenated viable rim that eventually regrew (FIG. 1A). Neither doxorubicin nor Doxil alone resulted in prolonged therapeutic effects in these mice. When Doxil was combined with *C. novyi*-NT spores, however, the effects were remarkable, resulting in complete regression of tumors in all mice (FIG. 1A) and cures in more than half of them (FIG. 1B). Notably, mice treated with *C. novyi*-NT and free doxorubicin at the same dose exhibited dramatic morbidity, with 100% of mice dying within 2 weeks, emphasizing the crucial role of liposomal encapsulation in reducing systemic toxicity (18).

EXAMPLE 3

Spores Plus Liposomes In Vivo in Second Model

To determine whether these pronounced anti-tumor effects could be observed in other tumor model systems, we treated human colorectal cancer xenografts [HCT116] growing in nude mice in the same way. As shown in FIGS. 1C and D, *C. novyi*-NT spores, when used in combination with Doxil, resulted in HCT116 tumor regressions similar to those observed with CT26 tumors. The dose of liposomal doxorubicin used in these tumor models was matched to those currently used in the clinic to treat cancer patients (19-21).

EXAMPLE 4

Distribution of Doxil in Vivo

Figure 2A:
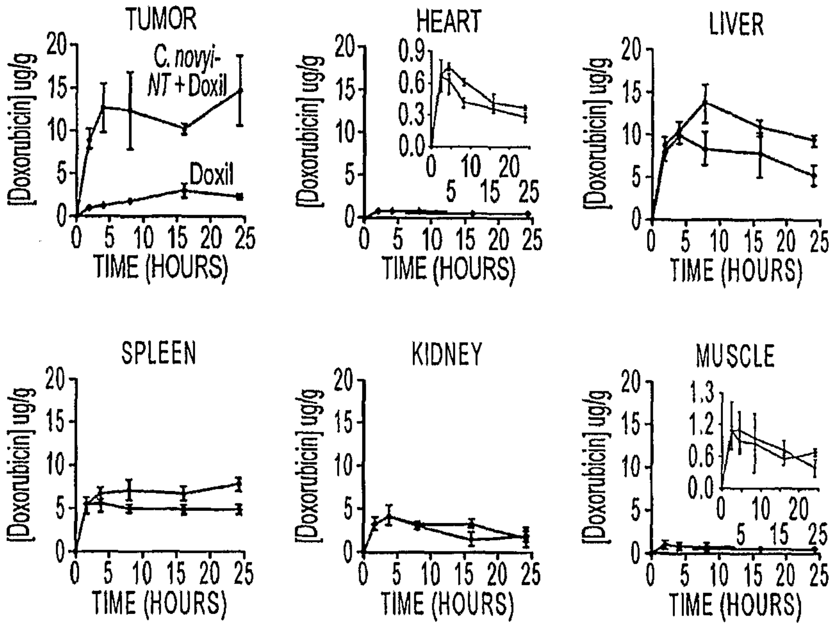
FIG. 2A-2B. Pharmacokinetic distribution of Doxil after treatment with *C. novyi*-NT.
Figure 2B:
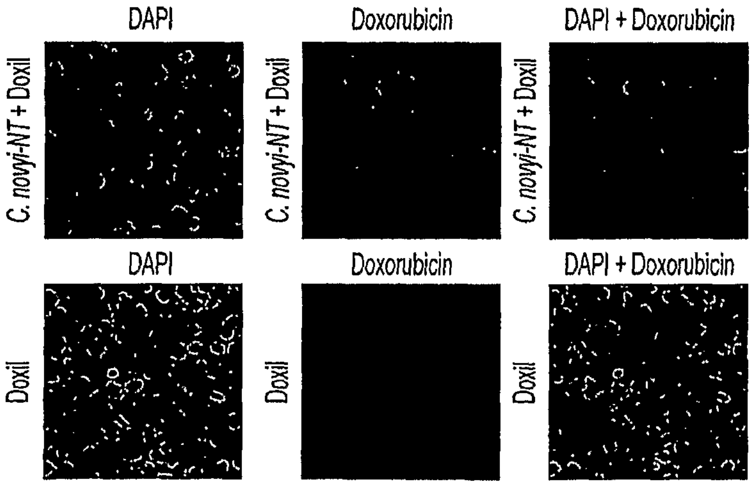

The synergistic effects observed in the experiments described above were presumably due to an increased concentration of doxorubicin in tumors as a result of *C. novyi*-NT infection. To substantiate this conjecture, the distribution of doxorubicin in mice receiving Doxil alone was compared with that in mice treated with Doxil plus *C. novyi*-NT spores. As shown in FIG. 2A, there was a remarkable increase in the intratumoral concentration of doxorubicin when Doxil was administered in the presence of *C. novyi*-NT. In contrast, the levels of doxorubicin in the heart, liver, spleen, kidney and muscle were similar in the presence or absence of spores (FIG. 2A). The doxorubicin found in infected tumors had been released from liposomes and was bound to tumor cell nuclei, as revealed by immunofluorescence (FIG. 2B). Note that the concentration of doxorubicin in conventionally-treated tumors was previously shown to be higher and more stable after administration of Doxil than after administration of doxorubicin (22). In effect, the administration of *C. novyi*-NT spores plus Doxil resulted in a greater than 100-fold increase in tumor drug exposure compared to that achieved with an equivalent dose of free doxorubicin, without increasing drug concentrations in normal tissues.

EXAMPLE 5

Attempted Identification of Likely Lipsome-Disrupting Factor

Figure 6A:
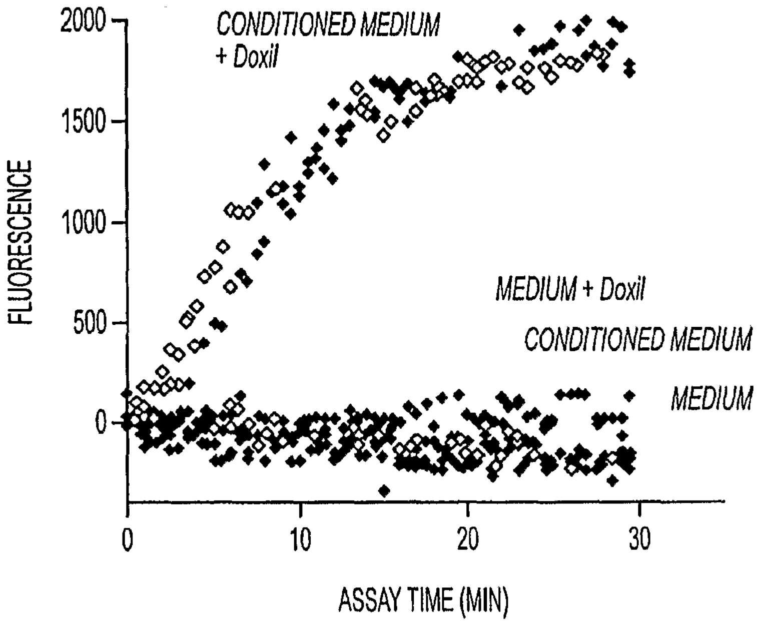
FIG. 6A-6B. Liposome-disrupting activity.
Figure 6B:
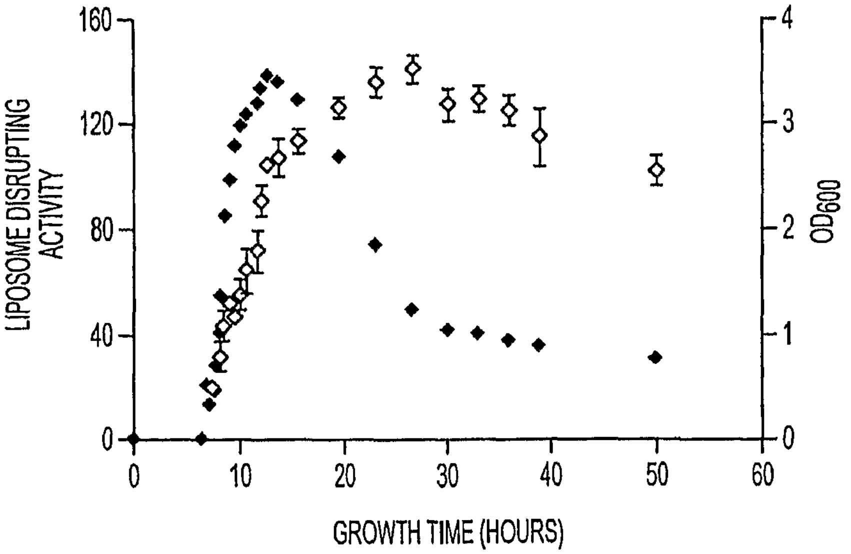

We next attempted to identify the mechanism underlying the ability of *C. novyi*-NT to release doxorubicin in tumors following injection of Doxil. We found that culture medium conditioned by the growth of *C. novyi*-NT contained a robust liposome-disrupting factor and that the concentration of this factor was maximum in late log phase (FIG. 6). We anticipated that this factor would be a phospholipase, as these enzymes are known to disrupt the lipid bilayers of liposomes as well as those of erythrocytes (17). Two phospholipase C enzymes have been purified from *C. novyi* and one of them possesses hemolytic activity (23-25). The *C. novyi*-NT genome contains four genes predicted to encode phospholipases (26). One of these four genes (NT01CX0979) encoded an extracellular phospholipase C protein (23, 25) which was expressed at high levels in growing bacteria (26).

Because *C. novyi*-NT has so far proved recalcitrant to transformation by exogenous DNA, we resorted to a different strategy to test the hypothesis that the liposome-disrupting factor was the phospholipase C NT01CX0979. Following MNNG-mediated mutagenesis, we plated ~10,000 bacteria on blood-agar plates and identified one colony which reproducibly lacked hemolytic activity. This clone was demonstrated by DNA sequencing to possess a 971G>A transition within the NT01CX0979 phospholipase C gene, resulting in a mutation from a well-conserved glycine to a glutamine (25). Surprisingly, the growth media of this hemolysis-negative clone retained its liposome-disrupting activity, indicating that this activity was not the result of NT01CX0979 or indeed of any other enzyme sufficient for hemolysis.

EXAMPLE 6

Identification of Liposome-Disrupting Factor and its Coding Sequence

Figure 3A:
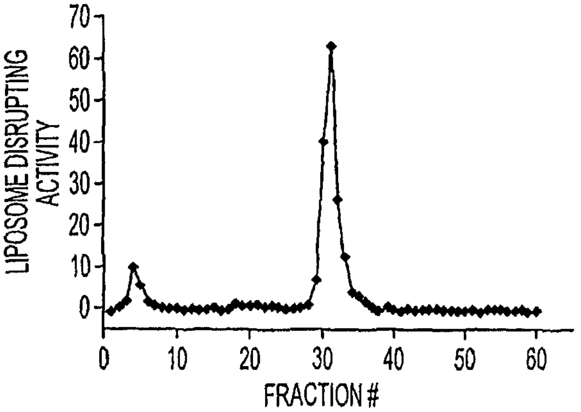
FIG. 3A-3C. Biochemical purification and Identification of Liposome-Disrupting activity.
Figure 3B:
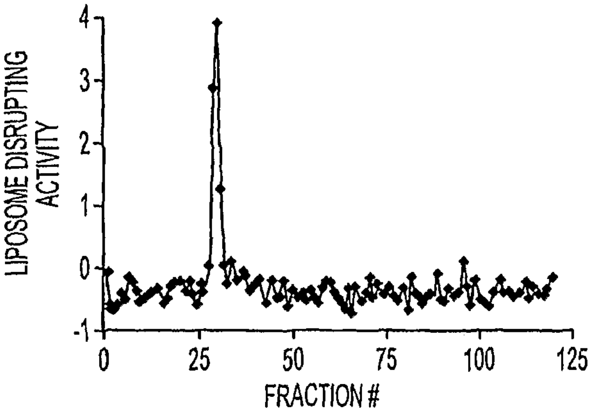
Figure 3C:
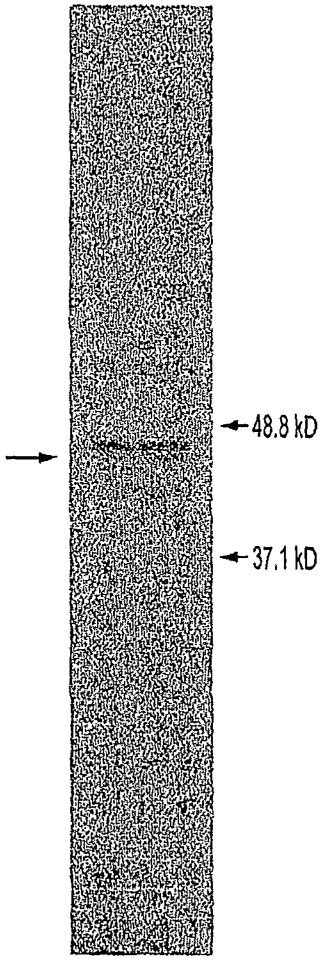

To identify the liposome-disrupting factor, we fractionated the growth medium from late log-phase *C. novyi*-NT via a combination of ammonium sulfate precipitation, ion exchange chromatography and gel filtration. A single, major peak of liposome-disrupting activity was observed (FIG. 3A, B). SDS-polyacrylamide gel electrophoresis revealed a predominant silver-staining band in the active fractions (FIG. 3C). This band was purified, digested by trypsin, and analyzed by liquid chromatography-tandem mass spectrometry. Using the *C. novyi*-NT genome as the reference, the polypeptide was found to be encoded by NT01CX2047, a putative lipase. The two extracellular lipases identified in the *C. novyi*-NT genome (NT01CX0630 and NT01CX2047) were not highly homologous to each other (47% aa identity) or to their closest counterparts in other bacteria (50~55% aa identity to a *C. tetani* lipase). The identification of the liposome-disrupting factor as the product of NT01CX2047 was consistent with information from the genomic analysis of *C. novyi*-NT, which revealed that NT01CX2047 was preferentially expressed in late log phase, was predicted to be extracellular, and was highly expressed in tumors after infection with *C. novyi*-NT (26).

EXAMPLE 7

Cloning of ORF of Liposome-Disrupting Factor

To examine the properties of the protein encoded by NT01CX2047, we cloned its ORF into an inducible expression vector which was then introduced into a genetically modified *E. coli* strain that permitted expression of *C. novyi*-NT genes (which have a codon usage very different than that of *E. coli*). Following induction of protein expression by IPTG, the transformed *E. coli* cells grew poorly, presumably because the gene product was toxic. Lysates from these cells were tested for lipase activity as measured by hydrolysis of 1,2-dioleoyl-3-pyrenedecanoyl-rac-glycerol. The NT01CX2047-expressing clones exhibited lipase activity, whereas clones cured of the vector (described below) did not (FIG. 4B). As a further control, a derivative was generated in which a stop codon was substituted for the serine residue at amino acid 127 (S127X). We also generated a mutant in which the serine at residue 127 was replaced by glycine (S127G). S127 is found within the highly-conserved GXSXG lipase motif and was predicted to be the essential catalytic serine responsible for lipase activity (27). Accordingly, both the S127G missense mutant and the S127X truncation mutant were devoid of lipase activity though each produced similar amounts of NT01CX2047 polypeptide (FIG. 4A, B). Interestingly, the non-catalytic S127G mutant exhibited the same poor growth as wild-type NT01CX2047, whereas the S127X mutant grew much more robustly. The apparent toxicity of the S127G mutant, which had no lipase activity, was puzzling but was illuminated by the experiments described below.

EXAMPLE 8

Genetic Separation of Lipase Activity and Liposome-Disrupting Activity

Figure 4D:
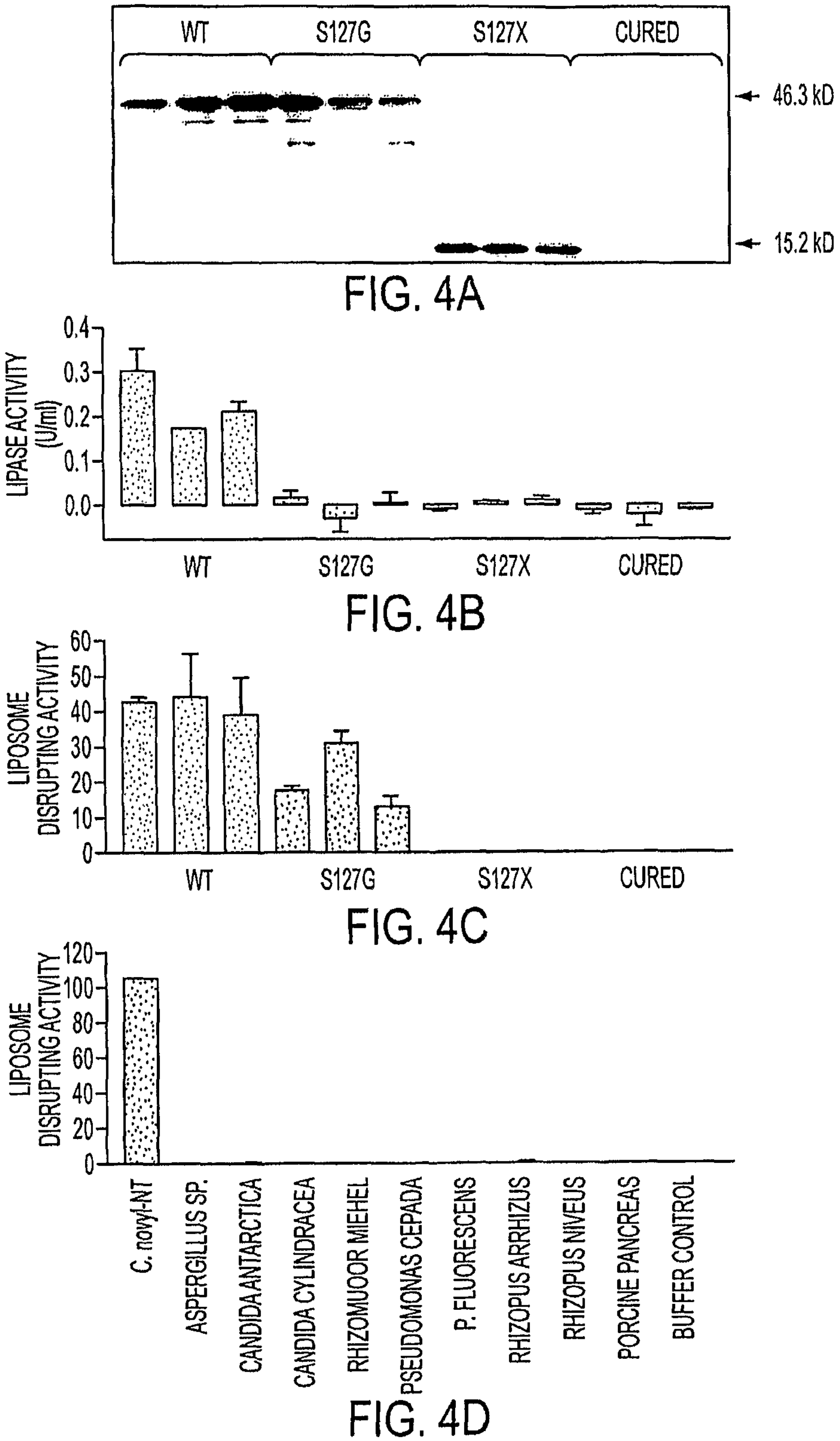
Figure 5A:
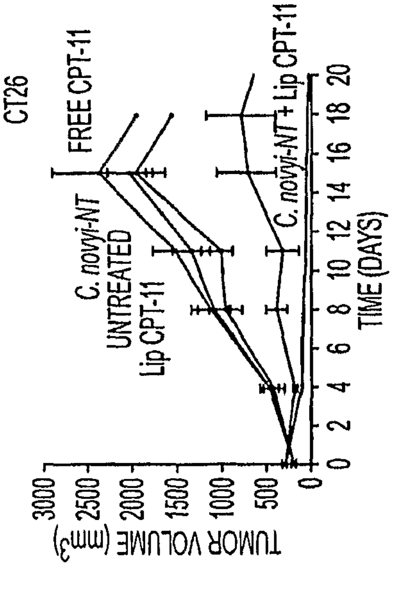
FIG. 5. Effects of treatment with *C. novyi*-NT plus liposomal CPT-11. Mice bearing the indicated tumors were treated on day 0 with various combinations of the indicated agents. Means and standard errors of data calculated from at least five mice per group are shown. The differences between *C. novyi*-NT plus Doxil and the other groups were significant ($p<0.0003$, log-rank test).
Figure 5B:
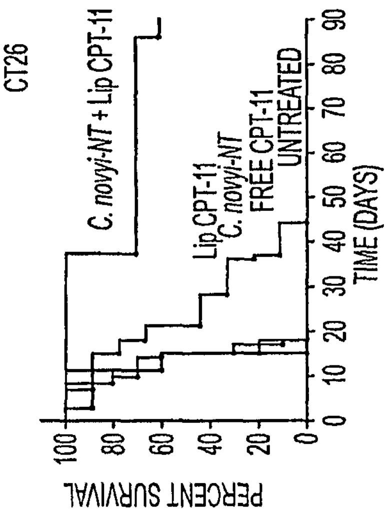
Figure 5C:
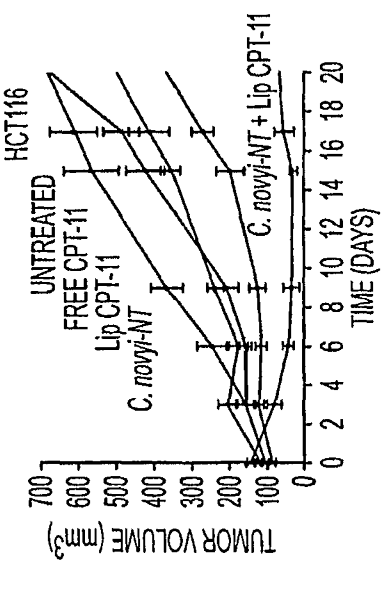
Figure 5D:
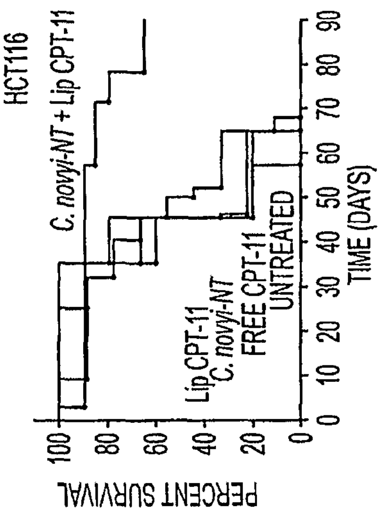

To test the liposome-disrupting activity of the lysates described above, we incubated them with liposomal doxorubicin. The strains containing the wild-type form of NT01CX2047 possessed potent activity in this assay (FIG. 4C). When this strain was cultured without selective antibiotics until the bacteria lost the expression vector by random segregation, the liposome-disrupting activity was lost (FIG. 4C). Moreover, the cells that had lost the plasmid were able to grow as robustly as the parental *E. coli* and the S127X mutant. As expected, the S127X truncation mutant had no detectable liposome-disrupting activity (FIG. 4C). Surprisingly, however, the S127G mutant, which was devoid of lipase activity, retained substantial liposome-disrupting activity (FIG. 4C). To determine whether the ability to disrupt liposomes was particular to the NT01CX2047 lipase of *C. novyi*-NT, we tested the liposome-disrupting activities of nine commercially available enzymes with well-defined lipase activity; none had significant liposome-disrupting activity (FIG. 4D).

EXAMPLE 9

Liposomes with Other Agents Also Effective

Accordingly, we tested liposomes containing CPT-11 (irinotecan), a topoisomerase inhibitor that, like doxorubicin, is widely used in cancer therapy. Single doses of liposomal CPT-11 were injected alone or 16 hours after *C. novyi*-NT administration, just as in the Doxil experiments. Both tumor types (CT26 in syngeneic mice and human colorectal cancer cell xenografts in nude mice) were relatively resistant to liposomal CPT-11 when injected alone. However, in the presence of spores, all tumors regressed and long-term cures were achieved in >60% of the mice (FIG. 5).

It was also notable in these and the liposomal doxorubicin experiments that the liposomase strategy was effective in small as well as in large tumors, with cures observed in tumors as small as 136 $mm^3$ in volume. In previous studies, small tumors proved to be resistant to bacteriolytic therapies because of the relatively small regions of necrosis within them (11). We suspect that liposomal drugs and *C. novyi*-NT spores are effective in combination because they mutually reinforce one another: the cytotoxic drug accumulated in the tumor through the EPR effect leads to necrosis and hypoxia, which leads to *C. novyi*-NT germination, which leads in turn to more release of the drug through liposomase.

Part of the release of doxorubicin from Doxil in tumors (FIG. 2) could theoretically be due to other enzymes released from *C. novyi*-NT or infected tumor cells. However, the major Doxil-disrupting factor secreted from *C. novyi*-NT is liposomase (FIG. 3) and its gene is expressed at high levels in infected tumors (26), suggesting that liposomase significantly contributes to the in vivo effects. Moreover, now that liposomase has been identified and cloned, it can be incorporated into other anti-cancer strategies. These strategies include cancer gene therapy employing viral or non-viral delivery systems and antibody-directed enzyme prodrug therapy (3, 4, 31, 32). In the past, such approaches have been limited by the small repertoire of prodrugs available and the necessity of getting the drug metabolized within a cell to exert a bystander effect on other tumor cells (31, 32). With liposomase, a large variety of "prodrugs" are already commercially available, as any chemotherapeutic agent that can be encapsulated in a liposome could theoretically be used. Multi-drug therapy, with each drug combined in a separate liposome, can also be envisaged. Finally, because liposomase is secreted and liposomes are external to the tumor cells, substantial bystander effects are to be expected.

REFERENCES

The disclosure of each reference cited is expressly incorporated herein.

1. D. D. Von Hoff, A.-R. Hanauske, in *Cancer Medicine* D. W. Kufe et al., Eds. (B C Decker, Inc., London, 2006) pp. 600-616.
2. C. Sawyers, *Nature* 432, 294 (Nov. 18, 2004).
3. S. V. Govindan, G. L. Griffiths, H. J. Hansen, I. D. Horak, D. M. Goldenberg, *Technol Cancer Res Treat* 4, 375 (August, 2005).
4. M. Yamamoto, D. T. Curiel, *Technol Cancer Res Treat* 4, 315 (August, 2005).
5. R. Kerbel, J. Folkman, *Nat Rev Cancer* 2, 727 (October, 2002).
6. R. K. Jain, D. G. Duda, J. W. Clark, J. S. Loeffler, *Nat Clin Pract Oncol* 3, 24 (January, 2006).
7. G. Thurston et al., *J Clin Invest* 101, 1401 (Apr. 1, 1998).
8. H. Hashizume et al., *Am J Pathol* 156, 1363 (April, 2000).
9. D. C. Drummond, O. Meyer, K. Hong, D. B. Kirpotin, D. Papahadjopoulos, *Pharmacol Rev* 51, 691 (December, 1999).
10. J. Fang, T. Sawa, H. Maeda, *Adv Exp Med Biol* 519, 29 (2003).
11. L. H. Dang, C. Bettegowda, D. L. Huso, K. W. Kinzler, B. Vogelstein, *Proc Natl Acad Sci USA* 27, 27 (2001).
12. N. Agrawal et al., *Proc Natl Acad Sci USA* 101, 15172 (Oct. 19, 2004).
13. R. M. Ryan, J. Green, C. E. Lewis, *Bioessays* 28, 84 (January, 2006).
14. A. M. Chakrabarty, *J Bacteriol* 185, 2683 (May, 2003).
15. P. Michl, T. M. Gress, *Curr Cancer Drug Targets* 4, 689 (December, 2004).
16. J. Theys et al., *Curr Gene Ther* 3, 207 (June, 2003).
17. J. Sakurai, M. Nagahama, M. Oda, *J Biochem* (*Tokyo*) 136, 569 (November, 2004).
18. D. Papahadjopoulos et al., *Proc Natl Acad Sci USA* 88, 11460 (Dec. 15, 1991).
19. H. H. Chou et al., *Gynecol Oncol* (Nov. 30, 2005).
20. R. E. Coleman et al., *Eur J Cancer* 42, 882 (May, 2006).
21. H. Varveris et al., *Strahlenther Onkol* 182, 125 (March, 2006).
22. H. D. Han et al., *Int J Pharm* 313, 181 (Apr. 26, 2006).
23. R. Taguchi, H. Ikezawa, *Biochim Biophys Acta* 409, 75 (Oct. 21, 1975).
24. R. Taguchi, H. Ikezawa, *Arch Biochem Biophys* 186, 196 (February, 1978).
25. K. Tsutsui et al., *J Bacteriol* 177, 7164 (December, 1995).
26. C. Bettegowda et al., *Science*, submitted (2006).
27. K. E. Jaeger, B. W. Dijkstra, M. T. Reetz, *Annu Rev Microbiol* 53, 315 (1999).

28. C. R. Alving, W. H. Habig, K. A. Urban, M. C. Hardegree, *Biochim Biophys Acta* 551, 224 (Feb. 20, 1979).
29. R. Blumenthal, W. H. Habig, *J Bacteriol* 157, 321 (January, 1984).
30. J. Sun et al., *Eur Biophys J* 33, 572 (November, 2004).
31. W. A. Denny, *Cancer Invest* 22, 604 (2004).
32. K. D. Bagshawe, S. K. Sharma, R. H. Begent, *Expert Opin Biol Ther* 4, 1777 (November, 2004).
33. L. H. Dang, C. Bettego);vda, D. L. Huso, K. W. Kinzler, B. Vogelstein, *Proc Natl Acad Sci USA* 27, 27 (2001).
34. S. A. Abraham et al., *Biochim Biophys Acta* 1565, 41 (Sep. 20, 2002).
35. S. A. Abraham et al., *Clin Cancer Res* 10, 728 (Jan. 15, 2004).
36. C. L. Messerer et al., *Clin Cancer Res* 10, 6638 (Oct. 1, 2004).
37. W. Wu et al., *Cancer Res* 66, 970 (Jan. 15, 2006).
38. H. O. Bagadi, M. M. Sewell, *Res Vet Sci* 15, 53 (1973).
39. A. Shevchenko, M. Wilm, O. Vorm, M. Mann, *Anal Chem* 68, 850 (Mar. 1, 1996).

We claim:

1. A composition comprising:

toxin-defective *Clostridium novyi* spores; and a liposome comprising an anti-tumor drug or biological agent.

2. A composition comprising:

a toxin-defective *Clostridium novyi* liposomase according to SEQ ID NO: 1 or according to SEQ ID NO: 1 with a substitution mutation in the GXSXG lipase motif at residues 160-164; and a liposome comprising an anti-tumor drug or biological agent.

3. The composition of claim 1 or 2 wherein the composition is formed in vivo in a non-human mammal.

4. The composition of claim 1 or 2 wherein the anti-tumor drug or biological agent is doxorubicin.

5. The composition of claim 1 or 2 wherein the anti-tumor drug or biological agent is irinotecan.

6. The composition of claim 1 or 2 wherein the anti-tumor drug or biological agent is an antibody.

7. The composition of claim 1 or 2 wherein the anti-tumor drug or biological agent is a polynucleotide.

8. The composition of claim 1 or 2 wherein the anti-tumor drug or biological agent is a polynucleotide in a viral vector.

9. The composition of claim 1 or 2 wherein the anti-tumor drug or biological agent is a polynucleotide in a non-viral vector.

10. The composition of claim 1 or 2 wherein the anti-tumor drug or biological agent is a protein.

11. The composition of claim 1 or 2 wherein the anti-tumor drug or biological agent is a cytokine.

12. A kit comprising:

a toxin-defective *Clostridium novyi* liposomase according to SEQ ID NO: 1 or according to SEQ ID NO: 1 with a substitution mutation in the GXSXG lipase motif at residues 160-164; and a liposome comprising an anti-tumor drug or biological agent.

13. A kit comprising:

toxin-defective *Clostridium novyi* spores; and a liposome comprising an anti-tumor drug or biological agent.

14. The kit of claim 12 or 13 wherein the anti-tumor drug or biological agent is doxorubicin.

15. The kit of claim 12 or 13 wherein the anti-tumor drug or biological agent is irinotecan.

16. The kit of claim 12 or 13 wherein the anti-tumor drug or biological agent is an antibody.

17. The kit of claim 12 or 13 wherein the anti-tumor drug or biological agent is a polynucleotide.

18. The kit of claim 12 or 13 wherein the anti-tumor drug or biological agent is a polynucleotide in a viral vector.

19. The kit of claim 12 or 13 wherein the anti-tumor drug or biological agent is a polynucleotide in a non-viral vector.

20. A method of treating a tumor bearing mammal, comprising:

administering to the tumor bearing mammal a first agent which is toxin-defective *Clostridium novyi* spores and a second agent which is a liposome comprising an anti-tumor drug or biological agent, whereby the tumor regresses or its growth is slowed or arrested.

21. A method of treating a tumor bearing mammal, comprising:

administering to the tumor bearing mammal a first agent which is a toxin-defective *Clostridium novyi* liposomase according to SEQ ID NO: 1 or according to SEQ ID NO: 1 with a substitution mutation in the GXSXG lipase motif at residues 160-164 and a second agent which is a liposome comprising an anti-tumor drug or biological agent, whereby the tumor regresses or its growth is slowed or arrested.

22. The method of claim 20 or 21 wherein the first agent and the second agent are administered sequentially.

23. The method of claim 20 or 21 wherein the first agent and the second agent are administered simultaneously.

24. The method of claim 20 or 21 wherein the anti-tumor drug or biological agent is doxorubicin.

25. The method of claim 20 or 21 wherein the anti-tumor drug or biological agent is irinotecan.

26. The method of claim 20 or 21 wherein the anti-tumor drug or biological agent is an antibody.

27. The method of claim 20 or 21 wherein the anti-tumor drug or biological agent is a polynucleotide.

28. The method of claim 20 or 21 wherein the anti-tumor drug or biological agent is a polynucleotide in a viral vector.

29. The method of claim 20 or 21 wherein the anti-tumor drug or biological agent is a polynucleotide in a non-viral vector.

30. A composition comprising an isolated and purified toxin-defective *Clostridium novyi* liposomase protein according to SEQ ID NO: 1 or according to SEQ ID NO: 1 with a substitution mutation in the GXSXG lipase motif at residues 160-164.

31. A conjugate protein comprising:

a toxin-defective *Clostridium novyi* liposomase protein according to SEQ ID NO: 1 or according to SEQ ID NO: 1 with a substitution mutation in the GXSXG lipase motif at residues 160-164; and a polypeptide ligand which binds to a receptor on a tumor cell.

32. The conjugate protein of claim 31 wherein the polypeptide ligand is a variable region of a heavy or light chain of an antibody.

33. The conjugate protein of claim 31 further comprising a linker peptide between the liposomase protein and the polypeptide ligand.

34. The conjugate protein of claim 31 wherein the polypeptide ligand comprises a variable region of a heavy chain and a variable region of a light chain of an antibody.

35. The conjugate protein of claim 34 which comprises a linker peptide between the variable region of the heavy chain and the variable region of the light chain.

36. The conjugate protein of claim 31 which is post-translationally conjugated.

37. The conjugate protein of claim 31 which is translated as a single polypeptide chain.

38. A polynucleotide which encodes the conjugate protein of claim 37.

39. A composition comprising an isolated and purified polynucleotide encoding a toxin-defective *Clostridium novyi* liposomase protein according to SEQ ID NO: 1 or according to SEQ ID NO: 1 with a substitution mutation in the GXSXG lipase motif at residues 160-164.

40. The composition of claim 39 wherein the polynucleotide comprises a nucleotide sequence according to SEQ ID NO: 2.

41. The composition of claim 39 wherein the polynucleotide comprises a vector.

42. The composition of claim 39 wherein the polynucleotide is in a viral vector.

43. The composition of claim 39 wherein the polynucleotide comprises a non-viral vector.

44. The composition of claim 39 wherein the polynucleotide comprises a promoter which is at least two-fold more transcriptionally active in a tumor than in a normal tissue.

45. The method of claim 20 wherein the tumor bearing mammal is a human.

46. The method of claim 20 wherein the tumor bearing mammal is a pet.

47. The method of claim 20 wherein the tumor bearing mammal is an agricultural animal.

48. The method of claim 20 wherein the tumor bearing mammal is a laboratory animal.

49. The method of claim 46 wherein the pet is a dog.

50. The method of claim 1 wherein the anti-tumor drug or biological agent is a topoisomerase inhibitor.

51. The method of claim 1 wherein the anti-tumor drug or biological agent is a DNA synthesis inhibitor.

* * * * *

UNITED STATES PATENT AND TRADEMARK OFFICE

CERTIFICATE OF CORRECTION

| | | |
|---|---|---|
| PATENT NO. | : | 8,444,963 B2 |
| APPLICATION NO. | : | 12/304178 |
| DATED | : | May 21, 2013 |
| INVENTOR(S) | : | Cheong et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1012 days.

Signed and Sealed this
Eighth Day of September, 2015

Michelle K. Lee
*Director of the United States Patent and Trademark Office*